United States Patent
Aksela et al.

(10) Patent No.: US 9,090,536 B2
(45) Date of Patent: Jul. 28, 2015

(54) PROCESS FOR THE PREPARATION OF A MIXTURE OF CHELATING AGENTS

(75) Inventors: Reijo Aksela, Espoo (FI); Jussi Rissanen, Turku (FI)

(73) Assignee: KEMIRA OYJ, Helsinki (FI)

( * ) Notice: Subject to any disclaimer, the term of this patent is extended or adjusted under 35 U.S.C. 154(b) by 100 days.

(21) Appl. No.: 13/639,575

(22) PCT Filed: May 31, 2011

(86) PCT No.: PCT/FI2011/050504
§ 371 (c)(1),
(2), (4) Date: Dec. 11, 2012

(87) PCT Pub. No.: WO2011/151517
PCT Pub. Date: Dec. 8, 2011

(65) Prior Publication Data
US 2013/0204035 A1    Aug. 8, 2013

(30) Foreign Application Priority Data
Jun. 2, 2010 (FI) ................................. 20105622

(51) Int. Cl.
C07C 213/06 (2006.01)
C07C 227/10 (2006.01)
C07C 227/06 (2006.01)
C07C 227/16 (2006.01)

(52) U.S. Cl.
CPC ............ C07C 227/10 (2013.01); C07C 227/06 (2013.01); C07C 227/16 (2013.01)

(58) Field of Classification Search
CPC ..................................................... C07C 213/06
USPC ................................. 560/171, 169
See application file for complete search history.

(56) References Cited

FOREIGN PATENT DOCUMENTS

| EP | 0775688 A1 | 5/1997 |
| EP | 1086944 A2 | 3/2001 |
| WO | 9745396 A1 | 12/1997 |
| WO | 9745585 A1 | 12/1997 |
| WO | 9946234 A1 | 9/1999 |
| WO | WO-99/46234 * | 9/1999 ............ C07C 213/06 |
| WO | 0052258 | 9/2000 |

OTHER PUBLICATIONS

International Search Report and Written Opinion dated Feb. 2, 2012.
Search Report for related Chilean patent application No. 3352-2012; dated Nov. 29, 2012; 9 pages; Chilean Patent Office.

* cited by examiner

*Primary Examiner* — Kamal Saeed
*Assistant Examiner* — Janet L Coppins
(74) *Attorney, Agent, or Firm* — Thomas Horstemeyer, LLP

(57) ABSTRACT

The present invention relates to a process for the preparation of a mixture of aspartic acid diethoxy succinate and an amino acid derivative of the general formula (I) wherein n is 1-10, m is 0 or 1, and R is hydrogen or an alkali metal or alkaline earth metal ion, comprising reacting maleate with diethanol amine under alkaline conditions in the presence of a lanthanoid catalyst to form aspartic acid diethoxy succinate followed by adding aspartic acid which reacts with unreacted maleate to form imino disuccinic acid, i.e. an amino acid derivative of formula (I) wherein m is 0, or by adding a diamine derivative of the general formula (II) NH2(CH2)nNH2 wherein n is as defined above, which reacts with unreacted maleate to form an amino acid derivative of formula (I) wherein m is 1 and n is as defined above.

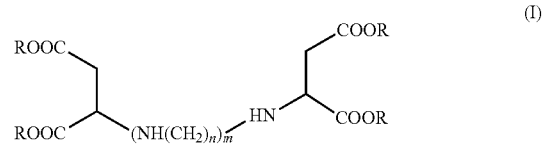

12 Claims, No Drawings

PROCESS FOR THE PREPARATION OF A MIXTURE OF CHELATING AGENTS

CROSS REFERENCE TO RELATED APPLICATION

This application is the 35 U.S.C. §371 national stage of PCT application entitled "Process for the Preparation of a Mixture of Chelating Agents," having serial number PCT/FI2011/050504, filed on 31 May 2011, which claims priority to Finland Application No. 20105622, filing date Jun. 2, 2010, which is incorporated by reference in its entirety.

TECHNICAL FIELD

The present invention relates to a process for the preparation of a mixture of aspartic acid diethoxy succinate and imino disuccinic acid or a mixture of aspartic acid diethoxy succinate and ethylene diamine disuccinic acid, which mixtures can be used as a chelating agent.

BACKGROUND OF THE INVENTION

WO 97/45396 discloses N-bis-and N-tris-[(1,2-dicarboxy-ethoxy)-ethyl]-amine derivatives including N-bis-[(1,2-dicarboxy-ethoxy)-ethyl]-aspartic acid (also called aspartic acid diethoxy succinate or AES), and the use of these derivatives as chelating agents of metals, especially in connection with pulp bleaching. These derivatives can be prepared by reacting a di- or triethanolamine with an alkali metal or alkaline earth metal salt of maleic acid in the presence of a catalyst such as lanthanoid compounds, a nickel compound or alkaline earth metal compounds, e.g. calcium hydroxide or magnesium hydroxide.

A drawback with the above synthesis of e.g. AES is that the reaction is relatively slow, the reaction time being about 12 to 16 hours, and that the reaction does not go to completion. A typical obtainable conversion from diethanol amine to AES is about 60 to 70%. A significant amount of the rather expensive maleic acid, typically up to about 40%, is left unreacted.

The aim of the present invention is to improve the process for the preparation of AES and to make the process for the preparation of AES more profitable. Another aim of the present invention is to provide a method for in situ preparation of mixtures of complexing agents.

SUMMARY OF THE INVENTION

According to the present invention it was surprisingly found that the unreacted maleic acid can easily and effectively be converted into another reactive ingredient by the addition of an amino compound into the reaction to yield an aspartic acid derivative, thereby utilizing the unreacted maleic acid. When aspartic acid or ethylene diamine is added, imino disuccinic acid (ISA) or ethylene diamine disuccinic acid (EDDS) are obtained respectively, yielding to a mixture of AES and ISA or a mixture of AES and EDDS.

DETAILED DESCRIPTION OF THE INVENTION

Thus, the present invention provides a process for the preparation of a mixture of aspartic acid diethoxy succinate and an amino acid derivative of the general formula:

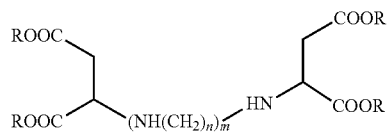

wherein n is 1-10, m is 0 or 1, and R is hydrogen or an alkali metal or alkaline earth metal ion, comprising reacting maleate with diethanol amine under alkaline conditions in the presence of a lanthanoid catalyst to form aspartic acid diethoxy succinate followed by adding aspartic acid which reacts with unreacted maleate to form imino disuccinic acid, i.e. an amino acid derivative of formula I wherein m is 0, or by adding an diamine derivative of the general formula

wherein n is as defined above, which reacts with unreacted maleate to form an amino acid derivative of formula I wherein m is 1 and n is as defined above.

A mixture of aspartic acid diethoxy succinate and Imino disuccinic acid or a mixture of aspartic acid diethoxy succinate and ethylene diamine disuccinic acid are obtained by reacting maleate with diethanol amine under alkaline conditions in the presence of a lanthanoid catalyst to form aspartic acid diethoxy succinate followed by adding aspartic acid which reacts with unreacted maleic acid to form imino disuccinic acid or by adding ethylene diamine which reacts with unreacted maleate to form ethylene diamine disuccinic acid.

The individual components of the mixture are preferably obtained as alkali metal salts or alkaline earth metal salts, but the components may also be obtained in acid form or may be converted from salts into acids. Preferred alkali metal salts are sodium or potassium salts, and preferred alkaline earth metal salts are calcium or magnesium salts.

A preferred embodiment of the invention relates to the preparation of a mixture of aspartic acid diethoxy succinate and imino disuccinic acid, wherein the process comprises reacting maleate with diethanol amine under alkaline conditions in the presence of a lanthanoid catalyst to form aspartic acid diethoxy succinate followed by adding aspartic acid which reacts with unreacted maleate to form imino disuccinic acid.

Following reaction scheme illustrates this preparation:

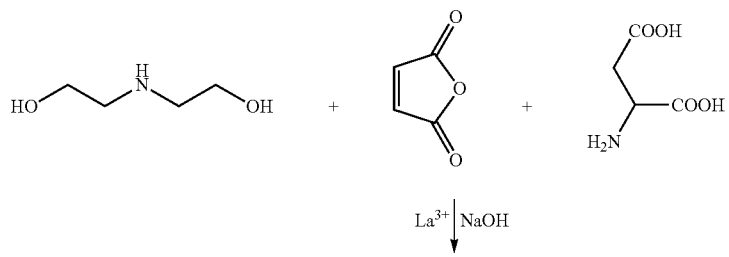

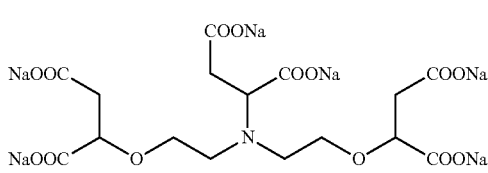
+
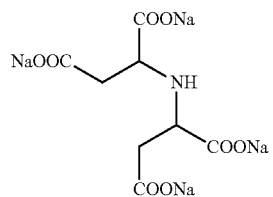

Another preferred embodiment of the invention relates to the preparation of a mixture of aspartic acid diethoxy succinate and ethylene diamine disuccinic acid, comprising reacting maleate with diethanol amine under alkaline conditions in the presence of a lanthanoid catalyst to form aspartic acid diethoxy succinate followed by adding ethylene diamine which reacts with unreacted maleate to form ethylene diamine disuccinic acid.

Following reaction scheme illustrates this preparation:

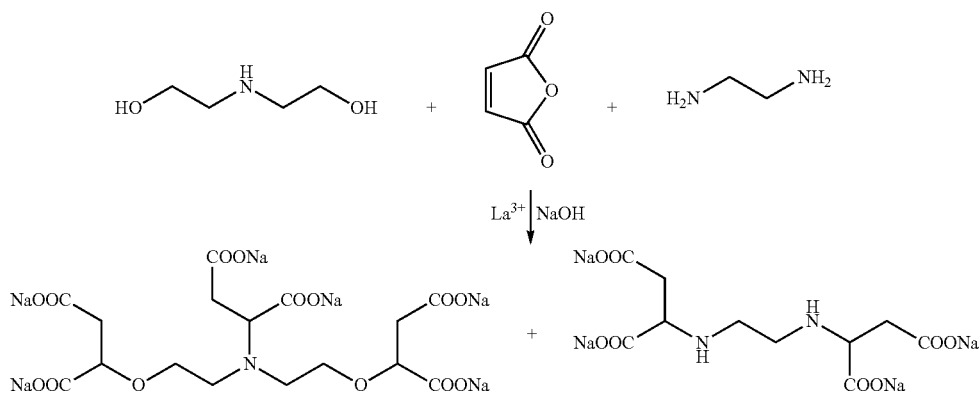

Preferably the amount of the diethanol amine is substoichiometric in relationship to the amount of the maleate. By varying this ratio is possible to obtain a desired amount of ISA or EDDS in the end product mixture.

The molar ratio of diethanol amine to maleate may be between 1:3.1 and 1:10, preferably between 1:3.5 and 1:4.

However, it is also possible to use e.g. a stoichiometric amount of diethanol amine in relationship to the amount of the maleate and add the ethylene diamine or aspartic acid after or before the AES reaction has reached its equilibrium.

Preferably the maleate and diethanol amine are reacted for a period of time for converting at least 30 mole % of diethanol amine into aspartic acid diethoxy succinate.

The molar ratio of the lanthanoid catalyst to maleate is preferably between 0.1:2.5 to 1:5, more preferably between 1:3 and 1:6.

The lantanoid (previously named lanthanide) series comprises the fifteen elements with atomic numbers from 57 to 71. Preferred lanthanoid catalysts are lanthanum (La), praseodymium (Pr), neodymium (Nd), europium (Eu), dysprosium Dy), erbium (Er) and ytterbium (Yb)

The elements of the lanthanoid series may be used in the form of oxides or salts including carbonates, nitrates, chlorides, maleates and octanates.

An especially preferred lanthanoid catalyst is a lanthanum catalyst including lanthanum(III)oxide and lanthanum(III) salts, such as lanthanum carbonate, lanthanum maleate, lanthanum nitrate, lanthanum chloride or lanthanum octanoate.

According to the invention the alkaline conditions may be obtained by dissolving maleic anhydride in water and adding an alkali metal compound or alkaline earth metal compound, such as an alkali metal hydroxide or carbonate or an alkaline earth metal hydroxide, carbonate or oxide.

A main advantage of the present invention is that unreacted maleate in the preparation of AES can be utilized for the preparation of ISA or EDDS preferably in the same reactor, thus making the process more profitable. The obtained mixture may be used as a chelating agent, e.g. in connection with pulp bleaching.

The invention will in the following be described in further detail by means of following non-limiting examples.

EXAMPLES

Example 1

Preparation of a Mixture of AES and ISA 98.06 g (1.000 mole) of maleic anhydride was dissolved in 258.40 g of water using a magnetic stirrer and heating to about 70° C. The aqueous maleic acid solution was transferred into a three-neck flask in a preheated oil bath. $La_2(CO_3)_3$ (0.263 moles) was added to the maleic acid solution. The addition was made slowly during about 5 minutes for controlling the effervescence caused by carbon dioxide. 31.14 g (0.252 moles) of diethanol amine was added into the reaction mixture. The temperature of the mixture was raised to about 90° C. The pH of the reaction solution was adjusted by adding 77.61 g (0.931 moles) of NaOH solution (aq. 48 wt %). The alkalinity of the reaction mixture was adjusted in connection with the second sample by adding 4.47 g (0.054 moles) of NaOH solution (aq. 48 wt %), whereby the pH raised to 8.55, and in connection with the third sample by adding 7.35 g (0.088 moles) of NaOH solution (aq. 48 wt %), whereby the pH i raised to 9.16.

After 12 hours from the start of the measurements 61.71 g (0.459 moles) of DL-aspartic acid was added. The alkalinity was restored by adding 74.00 g (0.888 moles) of NaOH solution (aq. 48 wt to pH 9.98 (T=93° C.). After the addition of aspartic acid and NaOH monitoring samples were taken with an interval of half an hour during six hours. The reason for that was the fast synthesis of ISA from aspartic acid and maleate especially in the catalyzed reaction. At each occasion two samples were taken. Into one of the samples warm 30% by weight $Na_2CO_3$ solution was added immediately to stop the reaction catalyzed by lanthanum at the sampling moment. The other sample was stored and frozen. The analysis was performed on the samples treated with the carbonate solution. During the synthesis samples were taken at 23 moments. The total duration of the synthesis was 60 hours of which the 12 first were pure synthesis of AES.

More accurate information regarding the conditions and concentrations of the reaction mixture are set forth in following table 1.

TABLE 1

| Sample | Reaction time (hh:mm:ss) | ISA (mole %) | AES (mole %) | Maleic acid (%) | pH | T °C. |
|---|---|---|---|---|---|---|
| 1 | 0:00:00 | | 2.69 | 100.00 | 8.13 | 97 |
| 2 | 4:00:00 | | 5.64 | 92.37 | 8.26 | 90 |
| 3 | 8:00:00 | | 18.03 | 78.90 | 8.42 | 92 |
| 4 | 12:15:00 | | 37.14 | 69.90 | 9.53 | 93 |
| 5 | 12:35:00 | 2.15 | 34.38 | 62.82 | 9.98 | 93 |
| 6 | 13:05:00 | 6.88 | 34.04 | 59.04 | 9.98 | 92 |
| 7 | 13:35:00 | 10.72 | 36.13 | 57.41 | 9.98 | 91 |
| 8 | 14:05:00 | 13.15 | 37.12 | 57.13 | 10.06 | 91 |
| 9 | 14:35:00 | 18.56 | 38.80 | 55.98 | 10.05 | 91 |
| 10 | 15:05:00 | 19.78 | 35.79 | 48.51 | 10.07 | 91 |
| 11 | 15:35:00 | 22.58 | 38.15 | 51.42 | 10.12 | 91 |
| 12 | 16:05:00 | 24.99 | 36.29 | 50.36 | 10.17 | 91 |
| 13 | 16:35:00 | 27.48 | 36.42 | 47.06 | 10.12 | 91 |
| 14 | 17:05:00 | 29.53 | 36.29 | 46.20 | 10.10 | 91 |
| 15 | 17:35:00 | 31.47 | 37.06 | 45.67 | 10.09 | 91 |
| 16 | 18:05:00 | 33.52 | 36.15 | 43.90 | 10.12 | 91 |
| 17 | 19:05:00 | 37.02 | 36.21 | 41.27 | 10.06 | 92 |
| 18 | 20:05:00 | 40.20 | 36.22 | 40.72 | 10.13 | 93 |
| 19 | 22:05:00 | 45.93 | 36.16 | 37.64 | 10.15 | 92 |
| 20 | 24:05:00 | 50.59 | 34.84 | 35.48 | 10.15 | 91 |
| 21 | 36:05:00 | 67.78 | 33.19 | 24.15 | 10.21 | 92 |
| 22 | 48:05:00 | 75.90 | 31.62 | 18.13 | 10.07 | 93 |
| 23 | 60:05:00 | | | | 10.16 | 92 |

The results in Table 1 show that when asparic acid is added to the reaction mixture, it stats reacting with unreacted maleate present in the reaction mixture, whereas the formation of additional AES is essentially stopped.

The results additionally show that after a reaction time of about 24 hours the yield of AES was about 35 mole % and the yield of ISA was about 50 mole % (based on the starting aspartic acid).

Example 2

Preparation of a Mixture of AES and EDDS 98.1 g (1.000 mole) of maleic anhydride was dissolved in 258.28 g of water using a magnetic stirrer and heating to about 70° C. The aqueous maleic acid solution was transferred into a three-neck flask in a preheated oil bath. $La_2(CO_3)_3$ (0.255 moles) was added as an aqueous slurry to the maleic acid solution (T=70° C.). The addition was made slowly during about 5 minutes for controlling the effervescence caused by carbon dioxide. Diethanol amine (30.96 g, 0.252 moles) was added into the reaction mixture. The temperature of the mixture was raised to about 90° C. The pH of the reaction solution was adjusted by adding 70.68 g (0.848 moles) of NaOH solution (aq. 48 wt %).

After about 12 hours from the start of the measurements 14.27 g (0.235 moles) of ethylene diamine was added. After the addition of ethylene diamine monitoring samples were taken with an interval of half an hour during six hours. Thereafter the sampling interval was extended. The reason for that was the fast synthesis of EDDS from ethylene diamine and maleate especially in the catalyzed reaction. At each occasion two samples were taken. Into one of the samples warm 30% by weight $Na_2CO_3$ solution was added immediately to stop the reaction catalyzed by lanthanum at the sampling moment. The other sample was stored and frozen. The analysis was performed on the samples treated with the carbonate solution. During the synthesis samples were taken at 23 moments. The total duration of the synthesis was 60 hours of which the 12 first were pure synthesis of AES.

More accurate information regarding the conditions and concentrations of the reaction mixture are set forth in following table 2.

TABLE 2

| Sample | Reaction time (hh:mm:ss) | EDDS (mole %) | AES (mole %) | Maleic acid (%) | pH | T °C. |
|---|---|---|---|---|---|---|
| 1 | 0:00:00 | | 2.76 | 100.00 | 8.04 | 96 |
| 2 | 4:00:00 | | 4.89 | 90.43 | 7.97 | 90 |
| 3 | 8:00:00 | | 10.90 | 84.03 | 8.30 | 91 |
| 4 | 12:00:00 | | 37.90 | 57.36 | 9.25 | 90 |
| 5 | 12:15:00 | 0.00 | 38.68 | 59.59 | 10.33 | 85 |
| 6 | 12:55:00 | 10.38 | 41.00 | 46.71 | 10.32 | 93 |
| 7 | 13:30:00 | | 40.78 | 39.12 | 10.57 | 92 |
| 8 | 14:00:00 | 35.89 | 40.83 | 34.40 | 10.62 | 92 |
| 9 | 14:30:00 | | 42.34 | 34.19 | 10.70 | 92 |
| 10 | 15:00:00 | 58.00 | 40.98 | 32.08 | 10.68 | 92 |
| 11 | 15:30:00 | | 38.55 | 30.65 | 10.68 | 92 |
| 12 | 16:00:00 | 73.42 | 38.76 | 28.99 | 10.68 | 92 |
| 13 | 16:30:00 | | 38.11 | 26.90 | 10.58 | 92 |
| 14 | 17:00:00 | | 38.46 | 26.61 | 10.59 | 92 |
| 15 | 17:30:00 | | 38.75 | 26.31 | 10.59 | 92 |
| 16 | 18:00:00 | 84.77 | 38.78 | 24.56 | 10.59 | 92 |
| 17 | 19:00:00 | | 39.15 | 22.76 | 10.52 | 91 |
| 18 | 20:00:00 | | 36.87 | 20.54 | 10.52 | 91 |
| 19 | 22:00:00 | | 38.78 | 19.42 | 10.44 | 91 |
| 20 | 24:00:00 | 94.84 | 36.66 | 17.54 | 10.37 | 90 |
| 21 | 36:00:00 | 100.00 | 32.90 | 12.17 | 10.19 | 90 |
| 22 | 48:00:00 | | 33.26 | 9.81 | 10.04 | 91 |
| 23 | 60:00:00 | | | | 9.89 | 91 |

The results in Table 2 show that when ethylene diamine is added to the reaction mixture, it stats reacting with unreacted maleate present in the reaction mixture, whereas the formation of additional AES is essentially stopped.

The results also show that the content of EDDS increased to over 50% of the theoretical maximum already after 2-3 hours after the addition of ethylene diamine.

The results additionally show that after a reaction time of about 36 hours the yield of AES was about 33 mole % and the yield of EDDS was 100 mole % (based on the starting ethylene diamine).

The invention claimed is:

1. A process for the preparation of a mixture of aspartic acid diethoxy succinate and an amino acid derivative of the general formula

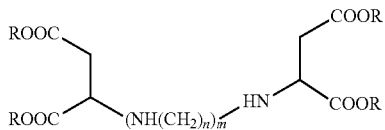

wherein n is 1-10, m is 0 or 1, and R is hydrogen or an alkali metal or alkaline earth metal ion, comprising reacting maleate with diethanol amine under alkaline conditions wherein the amount of the diethanol amine is substoichiometric in relationship to the amount of the maleate, in the presence of a lanthanoid catalyst to form aspartic acid diethoxy succinate followed by adding aspartic acid which reacts with unreacted maleate to form imino disuccinic acid, wherein the amino disuccinic acid is an amino acid derivative of formula I wherein m is 0, or by adding a diamine derivative of the general formula $$NH_2(CH_2)_nNH_2 \qquad II$$

wherein n is as defined above, which reacts with unreacted maleate to form an amino acid derivative of formula I wherein m is 1 and n is as defined above.

2. The process according to claim 1 wherein the molar ratio of diethanol amine to maleate is between 1:3.1 and 1:5.

3. The process according to claim 1, wherein maleate and diethanol amine are reacted for a period of time for converting at least 30 mole % of diethanol amine into aspartic acid diethoxy succinate.

4. The process according to claim 1, wherein the molar ratio of the lanthanoid catalyst to maleate is between 1:2.5 to 1:5.

5. The process according to claim 1, wherein lanthanoid catalyst is a lanthanum catalyst including lanthanum(III)oxide and lanthanum(III)salts.

6. The process according to claim 1, wherein the alkaline conditions are obtained by dissolving maleic anhydride in water and adding an alkali metal compound or alkaline earth metal compound.

7. The process according to claim 1, for the preparation of a mixture of aspartic acid diethoxy succinate and imino disuccinic acid, comprising reacting maleate with diethanol amine under alkaline conditions in the presence of a lanthanoid catalyst to form aspartic acid diethoxy succinate followed by adding aspartic acid which reacts with unreacted maleate to form imino disuccinic acid.

8. The process according to claim 1, for the preparation of a mixture of aspartic acid diethoxy succinate and ethylene diamine disuccinic acid, comprising reacting maleate with diethanol amine under alkaline conditions in the presence of a lanthanoid catalyst to form aspartic acid diethoxy succinate followed by adding ethylene diamine which reacts with unreacted maleate to form ethylene diamine disuccinic acid.

9. The process according to claim 2, wherein the molar ratio of diethanol amine to maleate is between 1:3.5 and 1:4.

10. The process according to claim 4, wherein the molar ratio of the lanthanoid catalyst to maleate is between 1:3 and 1:4.

11. The process according to claim 5, wherein lanthanoid catalyst is a lanthanum catalyst including lanthanum carbonate, lanthanum maleate, lanthanum nitrate, lanthanum chloride or lanthanum octanoate.

12. The process according to claim 6, wherein the alkaline conditions are obtained by dissolving maleic anhydride in water and adding an alkali metal hydroxide or carbonate or an alkaline earth metal hydroxide, carbonate or oxide.

* * * * *